US007364842B2

(12) United States Patent
Chao et al.

(10) Patent No.: US 7,364,842 B2
(45) Date of Patent: Apr. 29, 2008

(54) METHODS OF IDENTIFYING MODULATORS OF HUMAN RETROVIRUS REPLICATION

(75) Inventors: Sheng Hao Chao, San Diego, CA (US); Jeremy S. Caldwell, Cardiff, CA (US)

(73) Assignee: IRM, LLC, Hamilton (BM)

( * ) Notice: Subject to any disclaimer, the term of this patent is extended or adjusted under 35 U.S.C. 154(b) by 83 days.

(21) Appl. No.: 10/849,567

(22) Filed: May 18, 2004

(65) Prior Publication Data

US 2006/0171923 A1    Aug. 3, 2006

Related U.S. Application Data

(60) Provisional application No. 60/471,986, filed on May 19, 2003.

(51) Int. Cl.
*C12Q 1/00*    (2006.01)
*C12Q 1/70*    (2006.01)
*C12P 21/04*   (2006.01)

(52) U.S. Cl. .............................. 435/4; 435/5; 435/70.1; 435/70.3; 435/70.4

(58) Field of Classification Search .................. 435/7.1
See application file for complete search history.

(56) References Cited

U.S. PATENT DOCUMENTS

2001/0051635 A1    12/2001    Price et al.

FOREIGN PATENT DOCUMENTS

WO    WO 98/33067 A1    7/1998
WO    WO 98/47913 A2    10/1998

OTHER PUBLICATIONS

Mancebo et al. P-TEFb kinase is required for HIV Tat transcriptional activation in vivo and in vitro. Genes and Development, 1997, vol. 11, p. 2633-2644.*
Kimpton et al. Detection of Replication-Competent and Pseudotyped Human Immunodeficiency Virus with a Sensitive Cell Line on the Basis of Activation of an Integrated 3-Galactosidase Gene. Journal of Virology, Apr. 1992, vol. 66, No. 4, p. 2232-2239.*
Berthelsen, J., et al., "Prep1 a novel functional partner of Pbx proteins," *The EMBO Journal*, 1998, pp. 1423-1433, vol. 17, No. 5, Oxford University Press.
Chang, C-P., et al., "Meis Proteins are Major In Vivo DNA Binding Partners for Wile-Type but Not Chimeric Pbx Proteins," *Molecular and Cellular Biology*, Oct. 1997, pp. 5679-5687, vol. 17, No. 10, American Society for Microbiology.
Chao, S-H., et al., "Flavopiridol Inhibits P-TEFb and Blocks HIV-1 Replication," *The Journal of Biological Chemistry*, 2000, pp. 28345-28348, vol. 275, No. 37, U.S.A.
Chao, S-H, et al., "Identification of Homeodomain Proteins, PBX1 and PREP1, Involved in the Transcription of Murine Leukemia Virus," *Molecular and Cellular Biology*, Feb. 2003, pp. 831-841, vol. 23, No. 3, American Society for Microbiology.

Farnet, C., et al., "HIV-1 cDNA Integration: Requirement of HMG I(Y) Protein for Function of Preintegration Complexes in Vitro," *Cell*, Feb. 21, 1997, pp. 483-492, vol. 88, Cell Press.
Henderson, A., et al., "High-Mobility-Group Protein I Can Modulate Binding of Transcription Factors to the U5 Region of the Human Immunodeficiency Virus Type 1 Proviral Promoter," *Journal of Virology*, Nov. 2000, pp. 10523-10534, vol. 74, No. 22, American Society for Microbiology.
Hindmarsh, P., et al., "HMG Protein Family Members Stimulate Human Immunodeficiency Virus Type 1 and Avian Sarcoma Virus Concerted DNA Integration In Vitro," *Journal of Virology*, Apr. 1999, pp. 2994-3003, vol. 73, No. 4, American Society for Microbiology.
Knoepfler, P., et al., "The highest affinity DNA element bound by Pbx complexes in t(1;19) leukemic cells fails to mediate cooperative DNA-binding or cooperative transactivation by E2a-Pbx1 and Class I Hox proteins—evidence for selective targeting of E2a-Pbx1 to a subset of Pbx-recognition elements," *Oncogene*, 1997, pp. 2521-2531 vol. 14, Stockton Press.
Li, L., et al., "Modulation of Activity of Moloney Murine Leukemia Virus Preintegration Complexes by Host Factors In Vitro," *Journal of Virology*, Mar. 1998, pp. 2125-2131, vol. 72, No. 3, American Society for Microbiology.
Naghavi, M., "Regulation of HIV-1 provirus transcription," ISBN: 91-628-4865-8, Diss: 01:371, Jun. 2001, abstract only.
Chao, S-H. et al. "Identification of homeodomain proteins, PBX1 and PREP1, involved in the transcription of murine leukemia virus." Molecular and Cellular Biology, American Society for Microbiology. Feb. 2003. 23(3): 831-841.
Henderson, Angus et al. "High-mobility-group protein I can modulate binding of transcription factors to the U5 region of the human immunodeficiency virus type 1 proviral promoter." Journal of Virology. Nov. 2000. 74(22): 10523-10534.
Farnet, C. et al. "HIV-1 cDNA Integration: Requirement of HMG I(Y) Protein for Function of Preintegration Complexes In Vitro." Cell. Feb. 1997. 88: 483-492.
Hindmarsh, P. et al. "HMG protein family members stimulate human immunodeficiency virus type 1 and avian sarcoma virus concerted DNA integration in vitro." Journal of Virology. Apr. 1999. 73(4): 2994-3003.
Chang, C.P. et al. "Meis proteins are major in vivo DNA binding partners for wild-type but not chimeric Pbx proteins." Molecular Cell Biology. 1997. 17: 5679-5687.
Chao, S-H. et al. "Flavopiridol inhibits P-TEFb and blocks HIV-1 replication." J. Biol. Chem. 2000. 275: 28345-28348.
Li, L. et al. Modulation of activity of Moloney murine leukemia virus preintegration complexes by host factors in vitro. J. Virol. 72: 2125-2131.

(Continued)

*Primary Examiner*—Bruce R. Campell
*Assistant Examiner*—Louise Humphrey
(74) *Attorney, Agent, or Firm*—Townsend and Townsend and Crew LLP

(57) ABSTRACT

This invention relates to the discovery that the transcription factors Pbx1 and HMG I are involved in retrovirus, e.g., HIV, replication. Thus, the invention provides methods of identifying modulators of these proteins. Such modulators can be used as reagents in in vitro assays to modulate expression of retroviral sequences and may be used to inhibit HIV replication in vivo.

14 Claims, 11 Drawing Sheets

OTHER PUBLICATIONS

Knoepfler, P.S. et al. "The highest affinity DNA element bound by Pbx complexes in t(1;19) leukemic cells fails to mediate cooperative DNA-binding or cooperative transactivation by E2a-Pbx1 and class I Hox proteins—evidence for selective targeting of E2a-Pbx1 to a subset of Pbx-recognition elements." Oncogene. 1997. 14: 2521-2531.

Berthelsen, J. et al. "Prep1, a novel functional partner of Pbx proteins." The EMBO Journal. 1998. 17(5): 1423-1433.

Naghavi, M. "Regulation of HIV-1 provirus transcription." IBSN: 91-628-4865-8, Diss: 01:371, Jun. 2001, abstract only.

PCT International Search Report filing date May 19, 2004 for International Application No. PCT/US2004/015855.

* cited by examiner

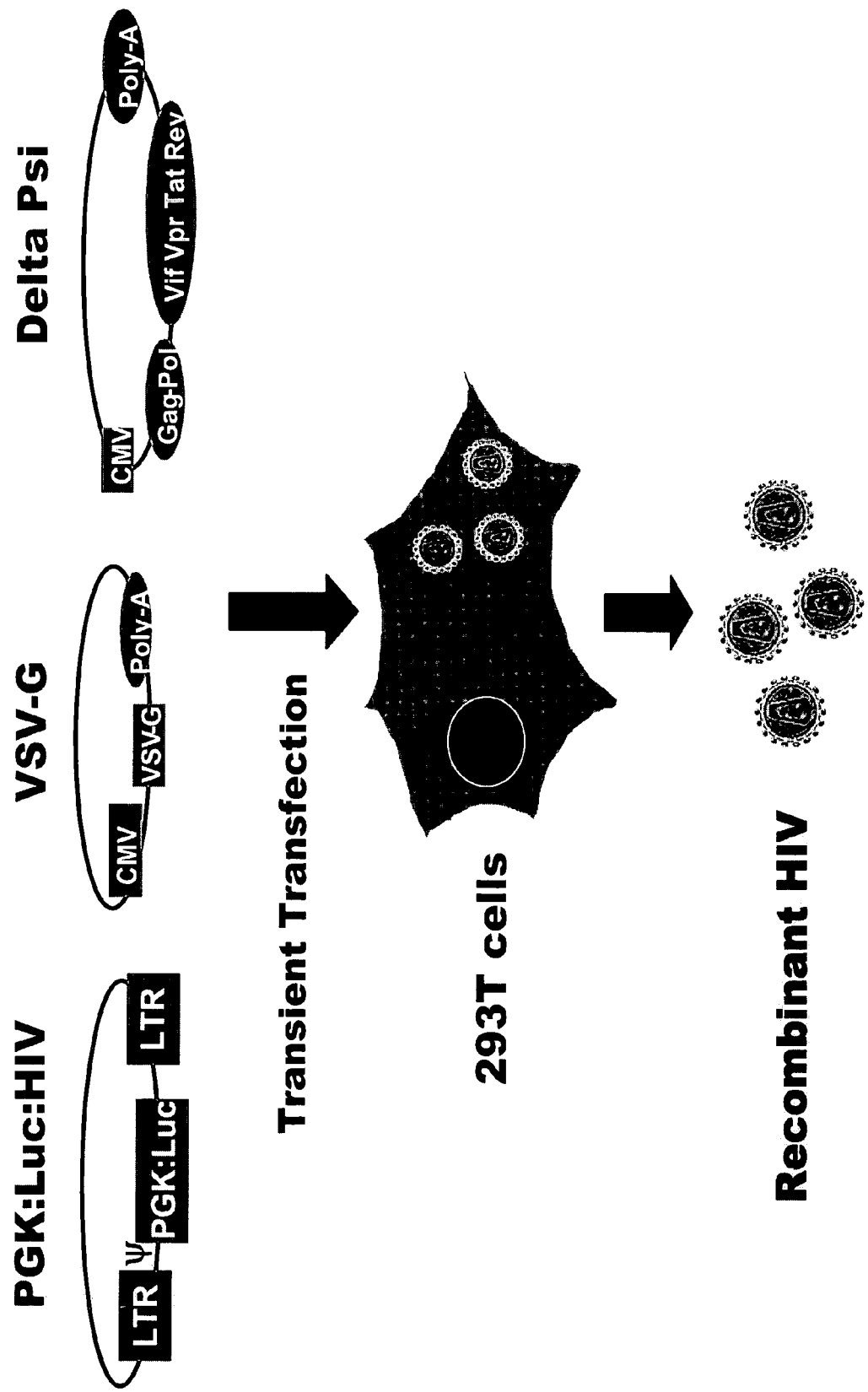

METHODS OF IDENTIFYING MODULATORS OF HUMAN RETROVIRUS REPLICATION

CROSS-REFERENCE TO RELATED APPLICATIONS

This application claims benefit of U.S. Provisional Application No. 60/471,986, filed May 19, 2003, which application is incorporated by reference herein.

FIELD OF THE INVENTION

This invention relates to the discovery that the transcription factors Pbx1 and HMG I family members, e.g., HMG I-C, are involved in replication of retroviruses that infect human cells such as HIV. Thus, the invention provides methods of identifying modulators of these proteins. Such modulators can be used as reagents in in vitro assays to modulate Pbx1- or HMG I-mediated retroviral gene expression, and moreover, may be used to inhibit HIV replication in vivo.

BACKGROUND OF THE INVENTION

Cyclin-dependent kinase inhibitors (CDKIs) have been shown to block human immunodeficiency virus (HIV) and herpes simplex virus. For example, the CDKI flavopiridol (Flavo) also has been shown to be a very potent anti-HIV compound (Chao, et al., J. Biol. Chem. 275:28345-28348, 2000). It has more recently been shown that three CDKIs, Flavo, purvalanol A (Purv), and methoxy-roscovitine (M-Ros), block Moloney murine leukemia virus (MLV) transcription events. Using gene expression microarray technology to further examine the inhibitory effects of CDKIs on MLV, several genes were identified that were down-regulated in 3T3 cells by CDKI treatment. These genes included the pre B-cell leukemia transcription factor 1 (Pbx1) and HMG I family members, e.g., HMG I-C (see, e.g., Chao et al., Mol. Cell. Biol. 23:831-841, 2003).

Pbx1 is a member of the TALE (three-amino acid loop extension) class of homeodomain transcription factors, which are components of heteroligomeric protein complexes that regulate gene expression. Pbx1 was first identified due to its involvement in a chromosomal translocation associated with pre-B cell human leukemia in which the E2A gene is truncated and fused to Pbx1 (Kamps et al., Cell 60:547-555, 1990; Nourse et al., Cell 60:535-545, 1990). It has also been implicated in the regulation of pancreatic development and diabetes mellitus (Kim et al., Nature Genet. 30:430-435, 2002). Pbx 1 binds the Pbx Consensus Element (PCE), TGATTGAC, as a heterodimer with other homeodomain factors such as MEIS1 or PREP1 (Chang, et al., Mol. Cell Biol. 17:5679-5687, 1997; Knoepfler & Kamps, Oncogene 14:2521-2531, 1997). In investigating the role of Pbx1 in the control of MLV transcription, PBX-binding regulatory elements were identified in the MLV long terminal repeat through which PBX1 and PREP1 heterodimers bind and positively regulate MLV transcription (see, e.g., Chao et al., Mol. Cell. Biol. 23:831-841, 2003).

High mobility group (HMG) proteins are members of a class of small nonhistone DNA-binding proteins that modulate chromatin structure and function. The HMG I(Y) family consists of three members (see, e.g., Bustin and Reeves, Prog. Nucleic Acids Res. Mol. Biol. 54:35-100, 1996): HMG I and HMG Y are alternatively spliced mRNA that are expressed from the same gene; HMG I-C is closely related, but transcribed from a different gene. It has been shown that HMG I family proteins can be involved in the integration of HIV, MLV, and Avian Sarcoma Virus integration in vitro (see, e.g., Farnet and Bushman Cell 88:483-492, 1997; Hindmarsh et al, J. Virol. 73:2994-3003, 1999;and Li et al. J Virol. 72:2125-2131, 1998). Additionally, it was reported that HMG I/Y modulates binding of transcription factors to the LTR of HIV (Henderson et al., J. Virol. 74:10523-10534, 2000).

BRIEF SUMMARY OF THE INVENTION

This invention provides novel targets for the identification of agents that regulate gene expression of retroviruses that infect humans. In particular, the invention provides methods of identifying compounds that modulate Pbx1 and HMG I activity. Such compounds can be used, for example, for the treatment of human retroviral infections, e.g., HIV-1 infection.

In one aspect, the invention provides a method of identifying a compound that inhibits replication of retrovirus that infects humans, the method comprising: contacting a candidate compound with a transcriptional regulator selected from the group consisting of a Pbx1 and an HMG I; determining whether the compounds inhibits Pbx1- or HMG I-mediated retroviral gene transcription, thereby identifying a compound that inhibits replication of the retrovirus. The retrovirus can be a lentivirus such as HTLV or HIV. In one embodiment, the retrovirus is HIV-1. Often, the method also comprises a step of selecting a compound that binds to the transcriptional regulator.

In some embodiments, the step of contacting the candidate compound with the transcriptional regulator comprises incubating the compound with the transcriptional regulator and a reporter construct comprising a Pbx1 or HMG I response element and a polynucleotide that encodes a detectable label. For example, in some embodiments the Pbx1 or HMG I response element is present in a regulatory sequence from a retrovirus that infects human cells e.g., a regulatory sequence that comprises an HIV-1 LTR. Typically, in the methods employing an HIV LTR, the incubation further comprises tat. In one embodiment, the incubation comprises contacting the compound with Magi indicator cells that express tat and comprise the transcriptional regulator and an HIV-1 LTR reporter construct. In another embodiment, the incubation comprises contacting the compound with HeLa cells that express tat and comprise the transcriptional regulator and an HIV-1 LTR reporter construct The transcriptional regulator is sometimes recombinant. Often, the regulator is Pbx1b, or HMG I-C.

In another aspect, the invention provides a method of identifying a compound that inhibits replication of a retrovirus that infects human cells, the method comprising: contacting a candidate compound with a transcriptional regulator nucleic acid that encodes a transcriptional regulator selected from the group consisting of a Pbx1 and an HMG I; and determining whether the compound inhibits Pbx1- or HMG I-mediated gene transcription, thereby identifying a compound that inhibits replication of the retrovirus that infects human cells. In one embodiment, the method further comprises selecting a compound that binds to the transcriptional regulator nucleic acid. The retrovirus can be a human immunodeficiency virus, e.g., HIV-1. In some embodiments, the transcriptional regulator is a Pbx1b or an HMG I-C.

In another embodiment, the step of contacting the candidate compound with the transcriptional regulator nucleic acid comprises incubating the compound with the nucleic acid and a reporter construct comprising a retroviral regulatory sequence such as an HIV-1 LTR. In some embodiments, the incubation further comprises tat.

In particular embodiments, the incubation comprises contacting the compound with Magi indicator cells that express tat and comprise an HIV-1 LTR reporter construct and the transcriptional regulator nucleic acid; or contacting the compound with HeLa cells that express tat and comprise an HIV-1 LTR reporter construct and the transcriptional regulator nucleic acid.

In some embodiments, the transcriptional regulator nucleic acid is comprised by an expression vector.

In some embodiments, the candidate compound is a nucleic acid such as an siRNA or an antisens RNA.

In another aspect, the invention provides a method of identifying a compound that inhibits replication of a retrovirus that infects human cells, the method comprising: incubating a candidate compound with an HMG I family member, e.g., HMG I/Y or HMG I-C; selecting a compound that inhibits replication of the retrovirus in a cell infected with the virus. In one embodiment, the retrovirus can be a human immunodeficiency virus, such as an HIV-1 virus.

In another aspect, the invention provides a method of inhibiting replication of a retrovirus that infects human cells, the method comprising administering a compound selected in accordance with the methods described herein. In one embodiment, the retrovirus is a human immunodeficiency virus such as HIV-1.

BRIEF DESCRIPTION OF THE DRAWINGS

FIGS. 5a and 5b provides a schematic of the system used to generate replication-defective HIV particles.

DETAILED DESCRIPTION OF THE INVENTION

Figure 1:
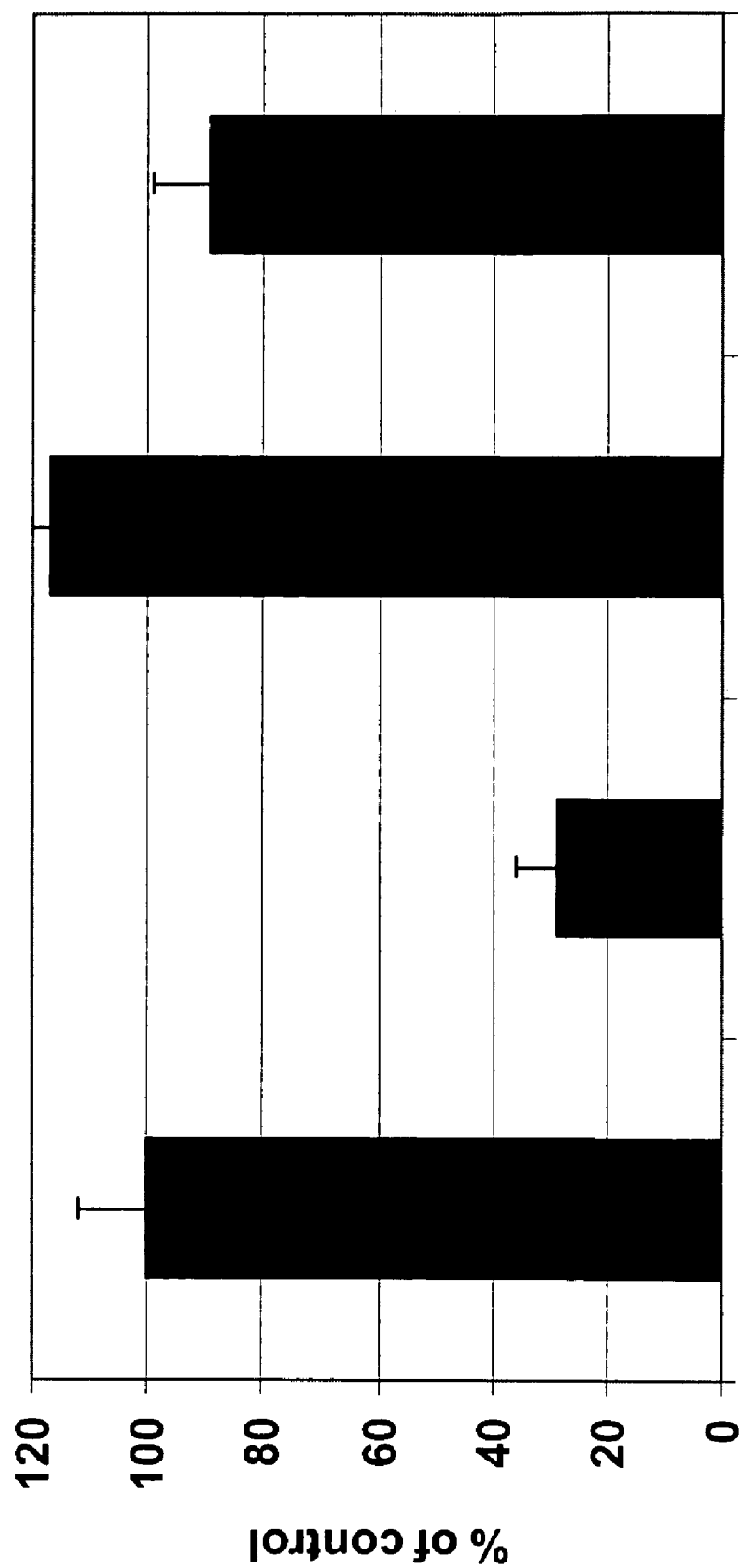
FIG. 1 provides exemplary data showing the effects of Pbx1 siRNA on HIV LTR-mediated gene expression in Magi cells ($\beta$-galactosidase assay).

The term "Pbx1" refers to both full-length and fragments of Pbx1 nucleic acid and polypeptide sequences as further described hereinbelow. There are two alternatively spliced forms of Pbx1, Pbx1 and Pbx1b. Pbx1b polypeptides lack the 83 C-terminal amino acid residues of the Pbx1a polypeptides.

An "HMG I family member" as used herein refers to an HMG I, HMG Y, or HMG I-C nucleic acid or polypeptide sequence. The term includes both full-length sequences and subsequences.

A "full length" Pbx1 or HMG I family protein or nucleic acid refers to a polypeptide or polynucleotide, or a variant thereof, that contains all of the elements normally contained in one or more naturally occurring, wild type Pbx1 polynucleotides or polypeptides. It will be recognized, however, that derivatives, homologs, and fragments of a Pbx1 or HMG I family member that modulate human retroviral replication, e.g., human retroviral transcription, can be readily used in the present invention.

A "human retrovirus" refers to a retrovirus, e.g., a lentivirus, that infects human cells. The term includes human T cell leukemia viruses, HTLV-1 and HTLV-2, and human lentiviral retroviruses, such as human immunodeficiency viruses, e.g., HIV-1 and HIV-2. A retroviral genome is generally organized into a 5' long terminal repeat (LTR), genes encoding structural proteins, e.g, gag, poly, and env; genes encoding accessory proteins (e.g., nef, vif, vpr, vpu in HIV) and regulatory proteins (e.g., rev and tat in HIV); and a 3' LTR. The viral LTR is divided into three regions, U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. The regions of human retroviral genomes that comprise LTRs are well known in the art (see, for example, "RNA Viruses: A Practical Approach" Alan J. Cann, Ed., Oxford University Press, 2000; and FIELDS VIROLOGY, Fourth Edition, Knipe et al, eds, Lippincott, Williams & Wilkins, 2001.

The term "tat" refers to a lentivirus regulatory protein that transactivates transcription from the viral LTR by binding to a hairpin structure, the TAR element, in the LTR.

The term "inhibits replication of a retrovirus that infects human cells" as used herein refers to inhibition of any process in human retrovirus replication. The term includes, but is not limited to, processes such as transcription of human retroviral genes. Other processes that may be involved in the replication of retrovirus include viral integration, RNA processing, and assembly of virus particles. Typically, the methods of the invention identify modulators that inhibit human retroviral gene transcription.

"Inhibitors" or "modulators" are used herein to refer to molecules that inhibit the ability of Pbx1 or an HMG I family member to promote replication of a virus that infects human cells. Typically, such modulators inhibit transcription mediated by Pbx1 or HMG I. Modulators include naturally occurring and synthetic ligands, antagonists, agonists, small chemical molecules and the like. Samples or assays comprising a Pbx1 or HMG I family member polypeptide or nucleic acid sequence and a test compound as described herein are treated with a potential modulator and are compared to control samples without the modulator to examine the extent of effect. Control samples (not treated with modulators) are assigned a relative activity value of 100%.

Inhibition of a Pbx1 is achieved when the interaction (e.g., binding, transcriptional activation etc.) compared to the control is less than about 80%, optionally 50% or 25, 10%, 5% or 1%.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complimentary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Cassol et al. (1992); Rossolini et al., Mol. Cell. Probes 8:91-98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The terms "identical" in the context of two or more Pbx1 or HMG I family member nucleic acids or polypeptide sequences, refer to two or more sequences or subsequences that are the same sequences. Two sequences are substantially identical if the two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides or polynucleotides that are substantially identical to the Pbx1 and HMG I polypeptides or polynucleotides, respectively, exemplified herein. Optionally, the identity exists over a region that is at least about 50 nucleotides or amino acids in length, or more preferably over a region that is 100 to 500 or 1000 or more nucleotides or amino acids in length.

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

DETAILED DESCRIPTION OF THE INVENTION

Introduction

The invention is based in part on the discovery that Pbx1 or HMG I family members, e.g., HMG I-C, modulate transcription of rretroviral genes, in particular genes of retroviruses that infect human cells. Although Pbx1 and HMG I family members, e.g., HMG I-C, have been implicated in the regulation of MLV gene transcription, a role in gene transcription of retroviruses that infect human cells had not previously been identified. Thus, the invention provides methods of identifying agents that inhibit Pbx1 or HMG I activity and thus inhibit replication of retroviruses that infect human cells.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

Pbx1 and HMG I Family Nucleic Acid and Protein Sequences

Pbx1 nucleic acids and proteins from human and other animals are known and publicly available (see, e.g., Kamps et al., *Cell* 60:547-555, 1990; and Nourse et al., *Cell* 60:535-545, 1990). For example, human Pbx1 amino acid and nucleic acid sequences are available under accession numbers NP_002576 and NM_002585, respectively; and murine Pbx1 amino acid and nucleic acid sequences are available under accession numbers NP_032809 and NM_008783, respectively.

In some embodiments, the Pbx1 or HMG I polypeptides used in the methods of the invention is a fragment or domain that essentially consists of, at least 15, often at least 20, 30, 40, or 50, 100 or more contiguous amino acids of a Pbx1 or HMG I protein having the amino acid sequence of one of the exemplary sequences provided above. Alternatively, the Pbx1 or HMG I polypeptides may have 60% identity, more often at least 70%, 80%, 85%, 90%, 95%, or greater identity to an exemplary Pbx1 or HMG I amino acid sequence.

Pbx1 proteins for use in this invention include fragments and variants that retain the ability to induce transcription of genes that are under the control of Pbx1 or HMG I response elements, such as genes of retroviruses that infect human cells. Such activity can be tested using assays well known to those of skill in the art. For example, a transcription assay that measures the ability of a Pbx1 polypeptide to activate a reporter construct that comprises a Pbx1 or HMG I response element, such as an retroviral LTR regulatory sequence, can be used to identify Pbx1 proteins for use in the invention. Those Pbx1 polypeptides variants or fragments that exhibit at least 50%, often 80%, 90%, 100% or greater activity relative to a reference Pbx1, e.g., human or mouse Pbx1, (Kamps et al., *Cell* 60:547-555, 1990; and Nourse et al., *Cell* 60:535-545, 1990) are typically used in the screening methods of the invention.

HMG I family proteins include HMG I/Y and HMG I-C proteins. HMG I nucleic acids and proteins are known (see, e.g., Friedmann, et al., *Nucleic Acids Res.* 21:4259-4267, 1993; Chau et al, *Nucleic Acids Res.* 23:4262-4266, 1995). Exemplary polynucleotide and amino acid sequences include human and mouse HMGI/Y sequences available under the accession numbers AAB00145, L17131, M23618 and J04179. Exemplary human and mouse HMG I-C polynucleotide and amino acid sequences are available under accession numbers NM_003483, Z31595, U28749, X58380, and X92518. As with Pbx1, HMG I fragments and variants that activate human retroviral transcription or facilitate viral replication may also be used in the methods of the invention.

Either naturally occurring or recombinant polypeptides of the invention can be purified for use in the assays of the invention. Naturally-occurring polypeptides of the invention can be purified from any source. Recombinant polypeptides can be purified from any suitable expression system.

The polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are being purified. For example, proteins having established molecular adhesion properties (e.g., polyhistidine) can be reversibly fused to a polypeptide of the invention. With the appropriate ligand, either protein can be selectively adsorbed to a purification column and then freed from the column in a relatively pure form. The fused protein may be then removed by enzymatic activity. Finally, polypeptides can be purified using immunoaffinity columns.

The polypeptides can then be used, for example, in in vitro binding assays to identify candidate compounds that bind to the polypeptide. Binding assays are typically performed in conjunction with assays to assess transcription. The binding and transcription assays may be performed in either order. In some embodiments, test compounds may be assayed for the ability to disrupt Pbx1 interactions with proteins with which it heterodimerizes, e.g., homeodomain proteins such as PREP1. For example, a candidate compound can be added, either before, after, or concurrently, to binding reaction comprising Pbx1 and PREP1. Inhibition of the Pbx1 binding interaction is achieved when the binding value relative to the control is about 90%, optionally 50%, optionally 25-0%.

Assessment of Transcription Levels

Transcription levels can be measured to assess the effects of a test compound on inhibition of Pbx1 or HMG I-mediated transcription. Typically, a host cell containing a Pbx1 or HMG I protein is contacted with a test compound in the presence of a Pbx1 or HMG-I-sensitive gene, e.g., a reporter expression construct that is controlled by a Pbx1 or HMG-I responsive gene element, and then the level of gene expression is measured. The gene element is typically from a retrovirus that infects human cells, such as an LTR. The amount of time to effect such interactions may be empirically determined, such as by running a time course and measuring the level of transcription as a function of time. The amount of transcription can be measured by using any method known to those of skill in the art to be suitable. For example, mRNA expression of a protein regulated by Pbx1 or HMG I can be detected using northern blots or PCR, or their polypeptide products can be identified using immunoassays. Alternatively, transcription based assays using reporter genes can be used as described in U.S. Pat. No. 5,436,128. The reporter genes can be, e.g., chloramphenicol acetyltransferase, luciferase, green fluorescent protein (GFP), β-galactosidase, and alkaline phosphatase.

The amount of transcription is then compared to the amount of transcription in either the same cell in the absence of the test compound. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Transcription is typically measured using a reporter construct that can reflect Pbx-1- or HMG-I-mediated gene transcription. For example, a reporter construct comprising a regulatory sequence from a gene from a retrovirus that infects human cells, e.g., an LTR, is introduced into the cell. The viral construct preferably comprises sequences from the LTR of a lentivirus that infects human cells, e.g., HIV-1. In some embodiments, the assay comprises other components, e.g., viral transactivating factors such as tat.

In assays to identify Pbx1 or HMG I inhibitors, samples that are treated with a potential inhibitors are compared to control samples to determine the extent of modulation. Control samples (untreated with candidate inhibitors) are assigned a relative activity value of 100. Inhibition of Pbx1 or HMG I is achieved when the activity value relative to the control is about 90%, optionally 50%, optionally 25-0%.

Additionally, Pbx1 or HMG I polypeptides can be used to identify inhibitors of retroviral gene transcription in an in vitro transcription assay. In such an assay, a Pbx1 or HMG I family member is added to an in vitro transcription reaction to assess the ability of a test compound to inhibit transcription that is induced by Pbx1 or HMG I.

Expression vectors that express the transcriptional regulatory protein, i.e., the Pbx1 or HMG I protein, and reporter constructs are generated using procedures well known in the art (see, e.g., Sambrook & Russell, and Ausubel, both supra). The cellular transcription assays can be performed using any cell that can support transcription of a gene from a retrovirus that infects human cells and a reporter construct that includes a Pbx1 or HMG I response element. Examples of suitable cell lines, such as Magi cells and HeLa cells that can be used in performing these assays, are described in the "EXAMPLES" section below.

In some embodiments, candidate compounds are evaluated for the ability to inhibit HMG-mediated HIV replication using an assay employing replication defective virus. Replication-defective recombinant HIV particles are generated using methodology known in the art, typically using multiple plasmids. For example, one plasmid encodes the core and enzymatic components of the virion that are derived from HIV-1. Another plasmid encodes an envelope protein(s), most commonly the G protein of vesicular stomatitis virus (VSV-G) because of its high stability and broad tropism. Another plasmid encodes the genome to be transferred to the target cell, e.g., a gene comprising a reporter construct expression cassette. The viral particles are then used to infect appropriate cells. The ability of a compound that targets an HMG I protein, e.g., HMG I-C, may be evaluated to determine whether it decreases reporter gene expression relative to a control.

Test Compounds and Screening

The compounds tested for selectivity toward particular populations of tumor cells can be any chemical compound (e.g., in some embodiments, small chemical compounds), or a biological entity, e.g., a macromolecule such as a protein, sugar, nucleic acid, or lipid. Thus, test compounds may be chemical molecules; combinatorial chemical libraries; nucleic acids, including oligonucleotides, anti-sense oligonucleotides, siRNAs, etc., polypeptides, including antibodies, antibody fragments, and short peptides; extracts, e.g., from natural sources; and the like.

The assays of the invention can be designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods are employed. These methods involve providing a combinatorial library, e.g., a chemical library, containing a large number of potential therapeutic compounds. Such "combinatorial chemical libraries" are then screened in one or more assays, such as transcriptional assays as described herein, to identify those library members (particular chemical species or subclasses) that display the desired characteristic activity, e.g., inhibition of Pbx1- or HMG I-mediated transcription. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., *Nature*

Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Candidate compounds include numerous chemical classes; however, often they are small organic molecules, generally having a molecular weight of more than about 100 and less than about 2, 500 daltons. Typical small molecules are less than about 2000, less than about 1500, less than about 1000, or less than about 500 daltons. The candidate compounds typically include functional groups necessary for structural interactions with proteins or nucleic acids, e.g., hydrogen bonding, and typically include at least an amine, carbonyl, hydroxyl, or carboxyl group, preferably at least two of the functional chemical groups. The candidate agents often comprise cyclical carbon or heterocyclic structures and/or aromatic or polyaromatic structures substituted with one or more of the above functional groups. Candidate compounds include peptides, saccharides, fatty acids, steroids, purines, pyrimidines, nucleic acids, and various structural analogs or combinations thereof.

High Throughput Assays

In the high throughput assays of the invention, it is possible to screen thousands of different modulators in a single day. In particular, each well of a microtiter plate, e.g., a 96, 384, or 1,536-well plate, can be used to run a separate assay against a selected potential modulator, or, if concentration or incubation time effects are to be observed, every 5-10 wells can test a single modulator. Thus, a single standard microtiter plate can assay a large number of modulators. For example, if 1536-well plates are used, then a single plate can easily assay from about 100-1500 different compounds. It is possible to assay many different plates, for example over 1 million wells per days, using high throughput systems, for example those described in WO02/31747. Thus, many thousands of compounds can be screened in a single day.

High throughput systems comprise automated components, including fluid transfer and dispensing devices. A number of fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to microtiter plates to set up several parallel simultaneous assays. Such a fluid transfer device typically comprises an array of receptacles arranged such that the outlets of the receptacle are aligned with wells on the microwell plate. The Robbins Hydra (Robbins, Scientific, Sunnyvale, Calif.) is another example of a fluid dispensing device that can also be used in high throughput screening systems. Other fluid manipulation devices may include those that incorporate positive displacement pumps and dispenser valves, such a Cartesian SynQUAD (U.S. Pat. No. 6,063,339, available from Cartesian Technologies, Inc., Irvine, Calif.).

As appreciated by one of skill in the art, the high throughput devices used in the screening methods may also comprise additional components such as an incubator, e.g., to provides particular growth conditions for cells.

Detectors may also be included in the high throughput assay system. The detectors may measure any physical property of a sample. For example, fluorescence, luminescence, phosphorescence, radioactivity, or any other physical property may be measured by the detector. Examples of detectors that are often used in cell-based high throughput screening assays include a Fluormetric Imaging Plate Reader System (FLIPR®), which is commercially available from Molecular Devices Corp. Sunnyvale, Calif.; and a chemiluminescent imaging plate reader (CLIPR™). Additional imaging systems are described, e.g., in WO00/17643.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image for high throughput systems.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. This type of apparatus is easily used for viewing any sample, e.g., by fluorescent or dark field microscopic techniques.

In one aspect of the present invention, test inhibitors can also comprise nucleic acid molecules that inhibit expression of a Pbx1 or HMG I family member. Conventional viral and non-viral based gene transfer methods can be used to introduce nucleic acids encoding engineered Pbx1 or HMG I polypeptides in mammalian cells or target tissues, or alternatively, nucleic acids that inhibit transcription or translation of Pbx1 or HMG I, such as siRNAs or anti-sense RNAs. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

In some embodiments, small interfering RNAs are tested. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, *Nature* 411:428-29 (2001); Elbahir et al., *Nature* 411:494-98 (2001); and Fire et al., *Nature* 391:806-11 (1998), where methods of making interfering RNA also are discussed. The siRNAs based upon the Pbx1 or HMG I family member sequences are less than 100 base pairs, typically 30 bps or shorter, and are made by approaches known in the art. Exemplary siRNAs according to the invention could have up to 29 bps, 25 bps, 22 bps, 21 bps, 20 bps, 19 bps, 15 bps, 10 bps, 5 bps or any integer thereabout or therebetween.

Formulation and Administration of Pharmaceutical Compositions

Agents that reduce or inhibit Pbx1 or HMG I activity can be administered directly to a human subject that is infected by a retrovirus. Administration is by any of the routes normally used for introducing a modulator compound into ultimate contact with the tissue to be treated and is well known to those of skill in the art.

The identified inhibitors can be administered to a patient at therapeutically effective doses to prevent, treat, or control retroviral disease, e.g., HIV infection. The compounds are administered to a patient in an amount sufficient to elicit an effective protective or therapeutic response in the patient. An effective protective or therapeutic response is a response that at least partially arrests or slows the symptoms or complications of the disease. An amount adequate to accomplish this is defined as "therapeutically effective dose." The optimal dose level for any patient will depend on a variety of factors including the efficacy of the specific modulator employed, the age, body weight, physical activity, and diet of the patient, and on a possible combination with other drug. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the modulator at various concentrations, as applied to the mass and overall health of the subject. Administration can be accomplished via single or divided doses.

The modulators of the invention may be used alone or in conjunction with other agents that are known to be beneficial in treating or preventing human diseases that are mediate by a retrovirus, e.g., HIV-1 infection. The modulators of the invention and an other agent may be co-administered, either in concomitant therapy or in a fixed combination, or they may be administered at separate times.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., Remington's Pharmaceutical Sciences, 17th ed. 1985)).

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intrathecally or into the eye (e.g., by eye drop or injection). The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

Delivery of Nucleic Acid Inhibitors

In some embodiments, the modulators are nucleic acids. Various methods are known to deliver nucleic acids to the target cells.

Non-viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Methods

The use of RNA or DNA viral based systems for the delivery of inhibitors of PBX1 or HMG I family proteins are known in the art. Conventional viral based systems for the delivery of Pbx1 or HMG I nucleic acid inhibitors can include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., a joint or the bowel. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with Pbx1 or HMG I nucleic acids and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

Kits

A modulator of Pbx1 and HMG I-mediated retrovirus gene expression is also useful for attenuating retrovirus gene expression in in vitro assays. For example, such compounds may be used to modulate expression of lentiviral vectors that comprise sequences that are responsive to Pbx1 and HMG I. The present invention therefore also provides for kits comprising inhibitors of Pbx1 and HMG I family members and optional components such as lentivirus expression vectors. Such kits can be prepared from readily available materials and reagents.

EXAMPLES

Example 1

Pbx1 Activates HIV Transcription

This example shows that PBX1 can function as a positive regulator of HIV transcription.

Figure 2:
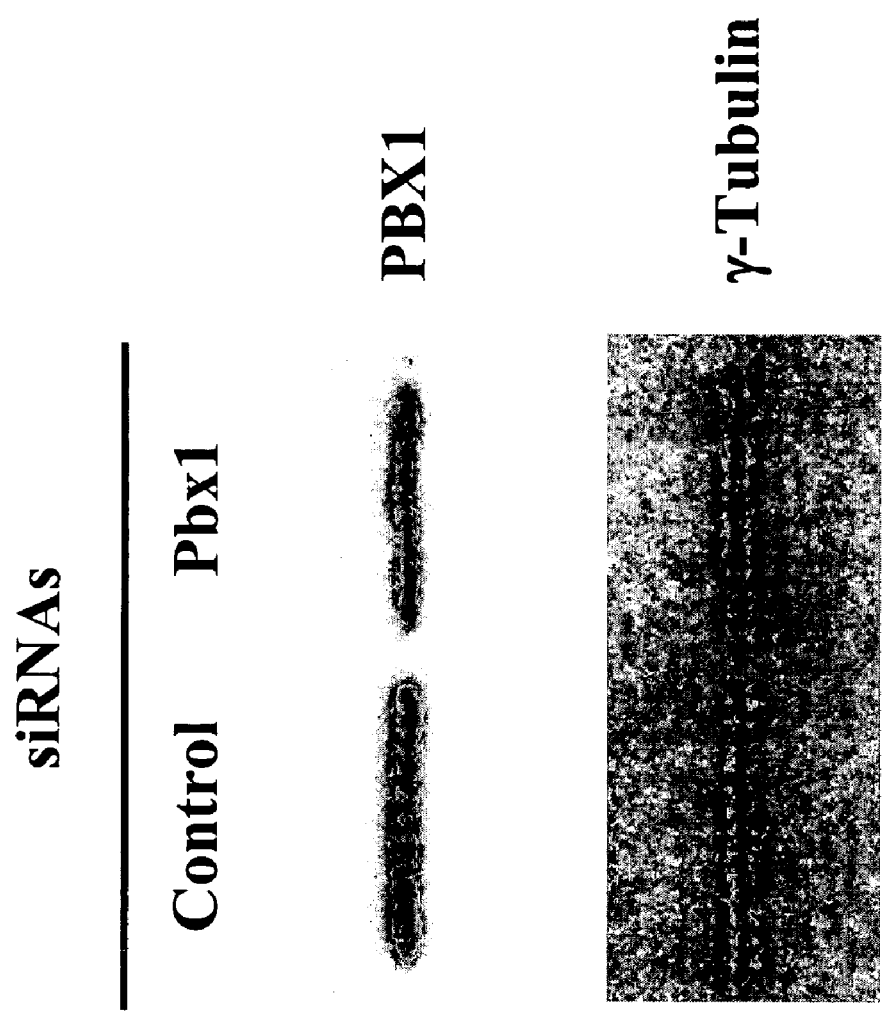
FIG. 2 provides exemplary data that show that Pbx1 protein is reduced in siRNA-transfected Magi cells.

The ability of Pbx 1 to mediate transcription of genes of retroviruses that infect human cells was investigated using Magi indicator cells (e.g., Kimpton and Emerman, *J. Virol.* 66: 2232-2239, 1992). The MAGI (Multinuclear Activation of a Galactosidase Indicator) cell line was derived from parental HeLa cells by introducing genes for CD4 and an HIV-1 LTR-driven β-gal reporter with an amphotropic retrovirus vector. This cell line exploits the ability of HIV-1 tat to transactivate the expression of a β-galactosidase reporter gene driven by the HIV-LTR. Magi cells were transiently transfected with an siRNA targeting Pbx1, Meis1, or Prep1. An siRNA called "Scramble siRNA" or "Scramble II Duplex," purchased from Dharmacon Research, Inc., that does not target any mammalian genes served as a negative control. The β-galactosidase activity was then assessed in the cultures. The results showed that β-gal activity was reduced in the cells that were transfected with the Pbx1 siRNA (Pbx1: AAGCCUGCCUUGUUUAAUGUG; SEQ ID NO:1) (FIG. 1). Western blot analysis of Pbx1 siRNA-transfected Magi cells confirmed that levels of Pbx1 protein were reduced in comparison to control cells transfected with firefly luciferase siRNA, which served as a negative control (FIG. 2). For the western blot analysis, cells were transiently transfected with the siRNAs targeting Pbx1 or firefly luciferase (control siRNA). Magi cells were lysed 48-60 hours after transfection and analyzed by western blot using antibodies against PBX1 or γ-tubulin proteins. The γ-tubulin was used as the loading control.

Figure 3:
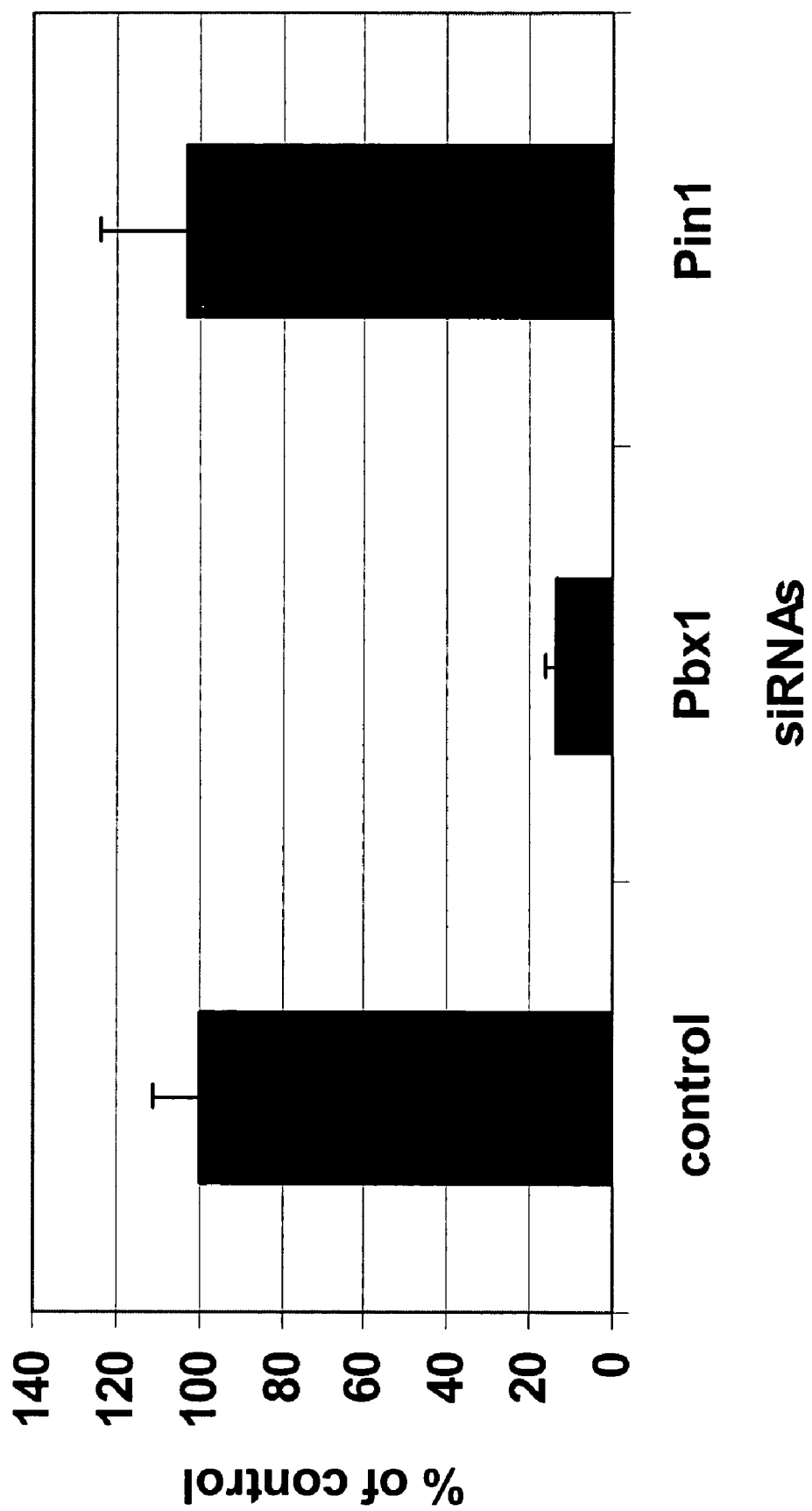
FIG. 3 provides exemplary data showing the effects of Pbx1 siRNA on viral replication of HIV-1 in Magi cells (reverse transcriptase assay).

Magi cells were transiently transfected with an siRNA targeting Pbx1 or Pin1. A Scramble siRNA was used as a negative control. Reverse transcriptase activity was then assessed. The results show that the cells that were transfected with the siRNA that targets Pbx1 exhibited greatly reduced activity of HIV reverse transcriptase relative to control and Pin1 siRNA-transfected cells (FIG. 3), suggesting that the viral replication of HIV was significantly blocked.

Figure 4:
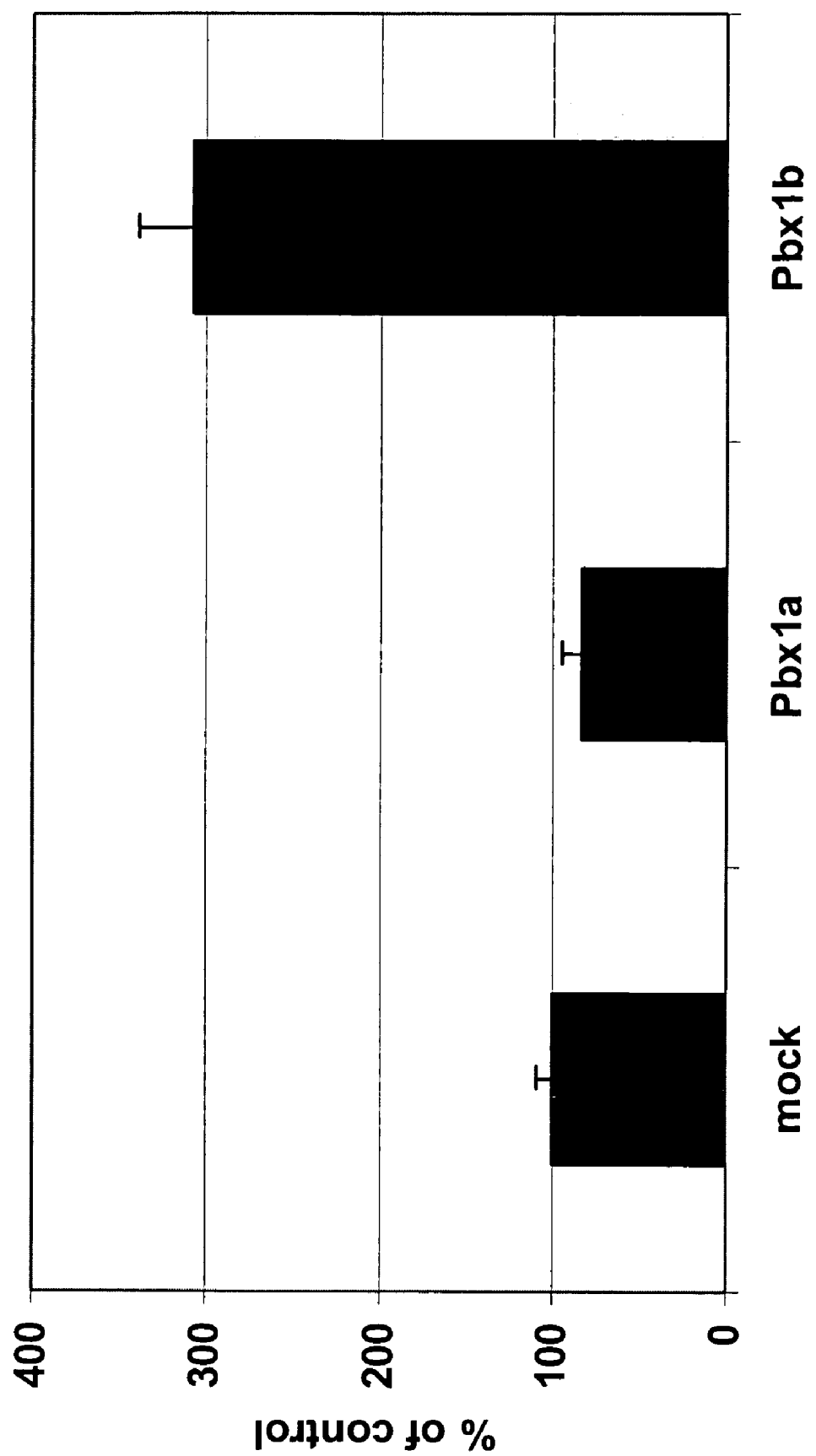
FIG. 4 provides exemplary data showing the effects of overexpressing Pbx1a/b on HIV Tat transactivation.

The ability of Pbx1 to induce tat-mediated transactivation of HIV-LTR was then determined. This was analyzed using HeLa cells that were transfected with a reporter construct containing a luciferase reporter gene linked to an HIV-1 LTR (HIV-LTR-LUC), a construct that expresses Tat (CMV-Tat) and an expression plasmid that expresses the polypeptide of interest. Cells were transiently co-transfected with HIV-LTR-Luc, CMV-Tat, and an expression plasmid, CMV-Pbx1a or CMV-Pbx1b. A CMV plasmid that did not contain any coding sequences served as a negative control. The results showed that overexpression of Pbx1b, but not Pbx1a, induced HIV Tat transactivation (FIG. 4).

Example 2

HMG I Proteins are Involved in Replication of Retroviruses that Infect Human Cells This example shows that HMG I family proteins are involved in HIV replication in vivo.

Figure 5B:
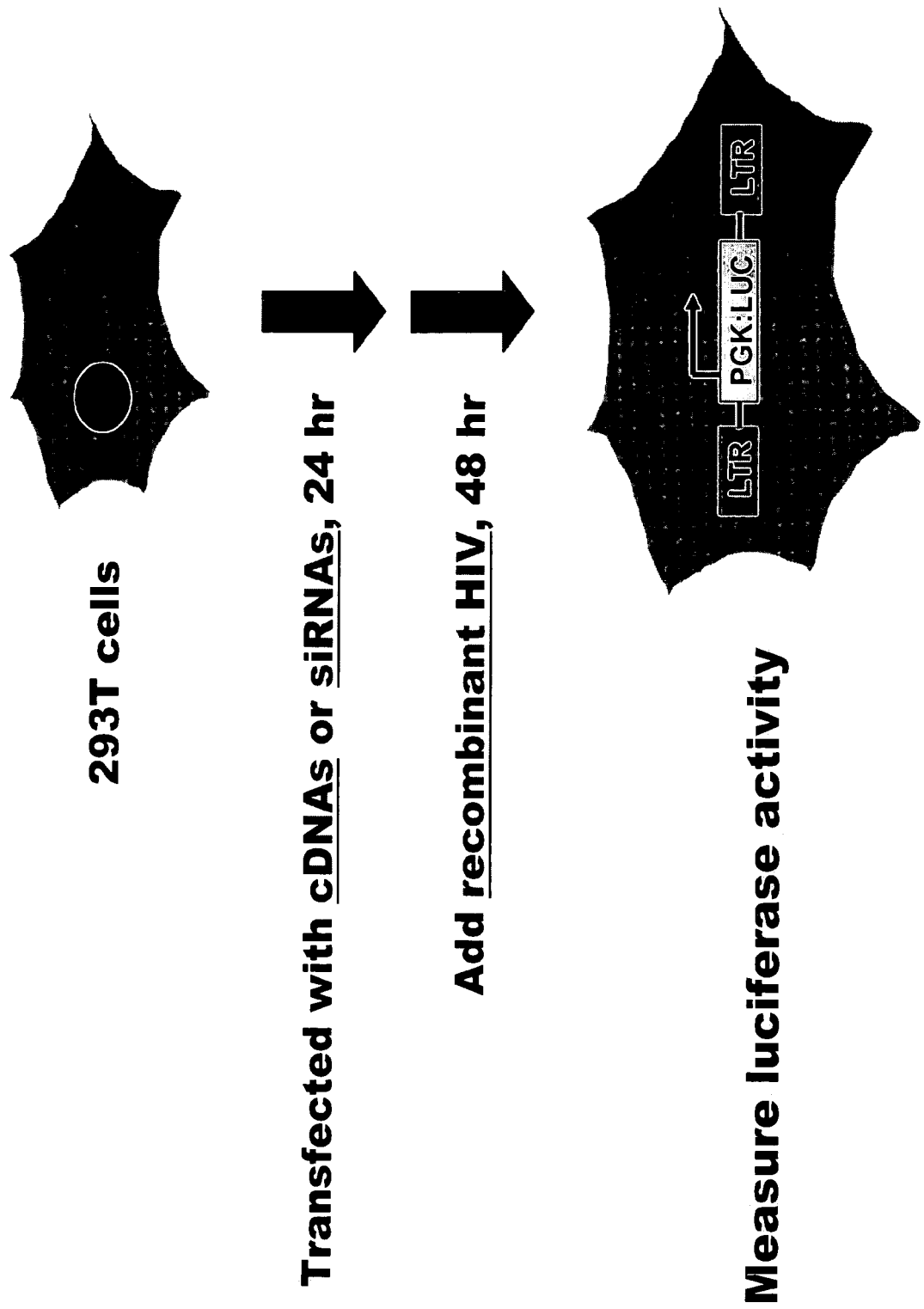

A recombinant HIV assay was used to assess the role of HMG I proteins in HIV replication. Pseudotyped recombinant HIV particles were generated by transient transfection of 293T cells using a three-plasmid expression system (FIGS. 5a and 5b). The cells were co-transfected with a packaging construct, PGK:LUC:HIV, that contains a psi packaging sequence, and a phosphoglycerate kinase-1 promoter/firefly luciferase gene expression cassette flanked by HIV-1 5' and 3' LTRs; a VSV-G expression plasmid that provides a vesicular stomatitis virus envelope protein; and a Delta Psi expression plasmid, which provides Gag-pol and regulatory genes.

Figure 6:
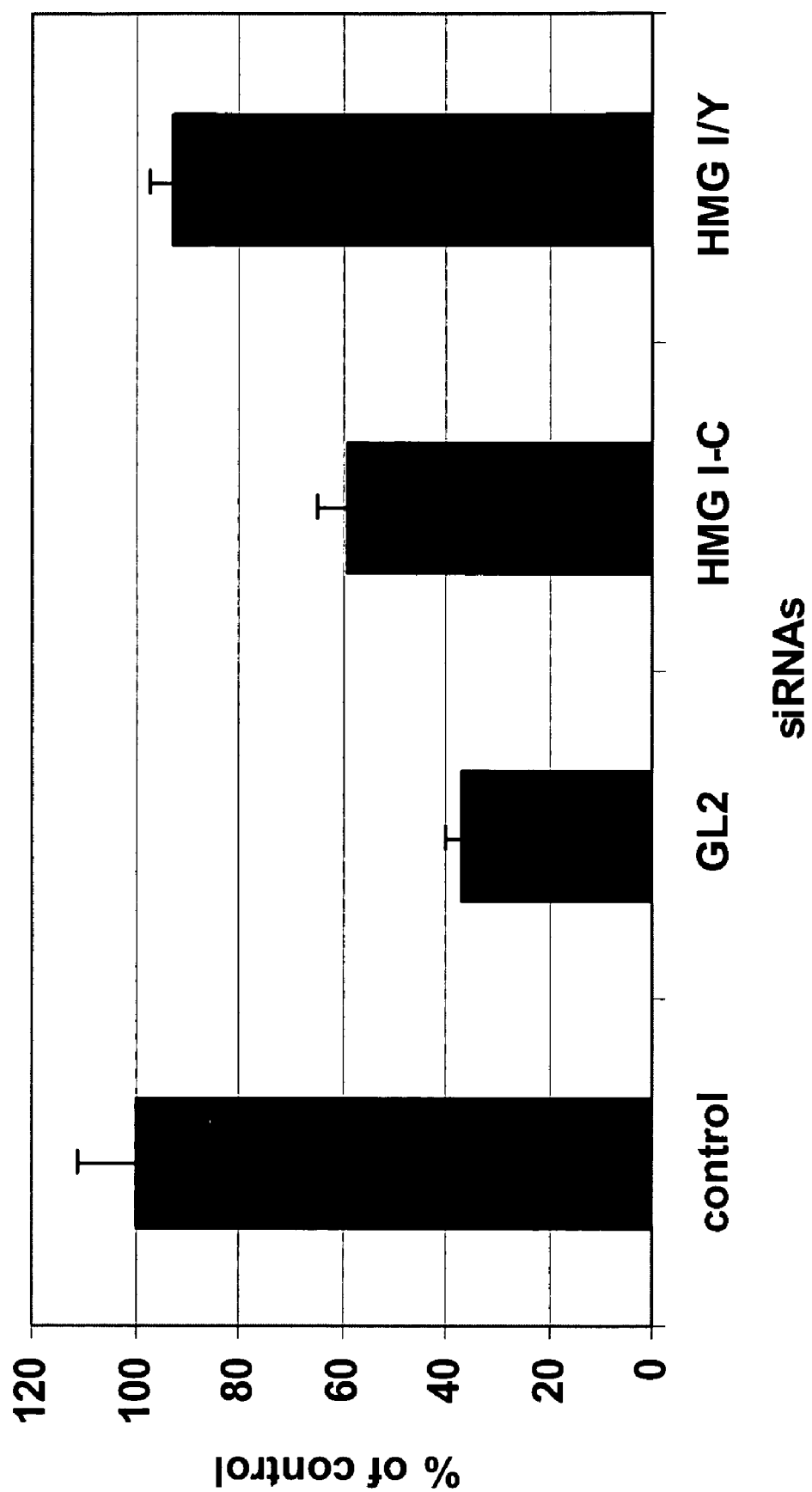
FIG. 6 provides exemplary data showing the effects of siRNAs targeting HMG I/Y and HMG I-C on HIV LTR-mediated gene expression in 293T cells that contain a reporter construct in which luciferase expression is controlled by an HIV LTR.

The role of HMG I proteins in HIV replication was assessed by transfecting 293T cells with siRNAs that target HMG I (HMG I/Y: AAGUGCCAACACCUAAGAGAC; SEQ ID NO:2), HMG I/Y (HMG I-C: AAGCAGCU-CAAAAGAAAGCAG; SEQ ID NO:3), or luciferase. A Scramble siRNA was used as a negative control After 24 hours, the transfected cells were infected with recombinant HIV. After 48 hrs, luciferase activity was measured. The results showed that cells that were transfected with HMG I-C and the siRNA targeting luciferase exhibited reduced reporter activity relative to control cells (FIG. 6).

Figure 7:
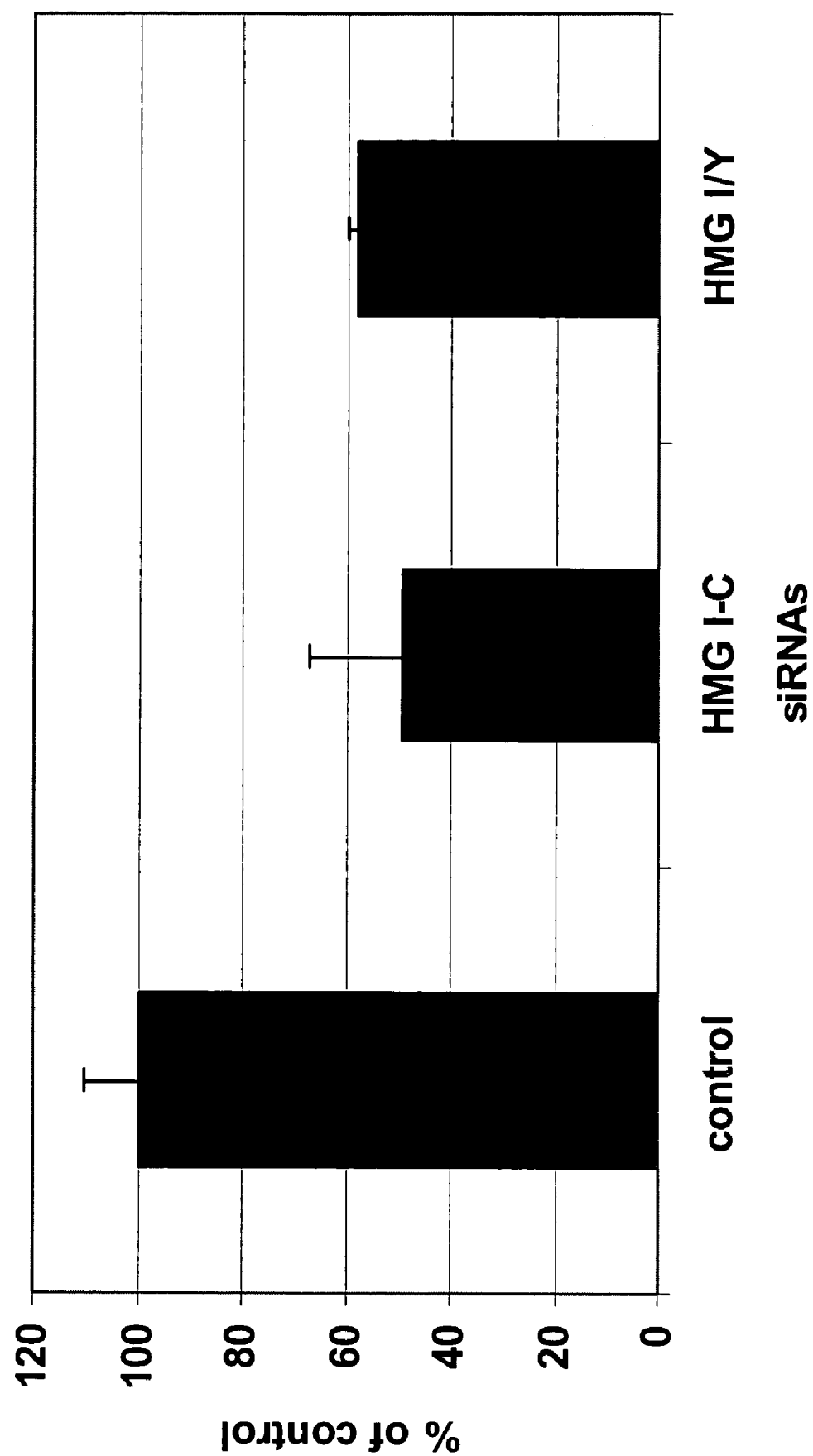
FIG. 7 provides exemplary data showing the effect of HMG I/Y and HMG I-C siRNA molecules on HIV LTR-mediated gene expression in Magi cells ($\beta$-galactosidase assay).
Figure 8:
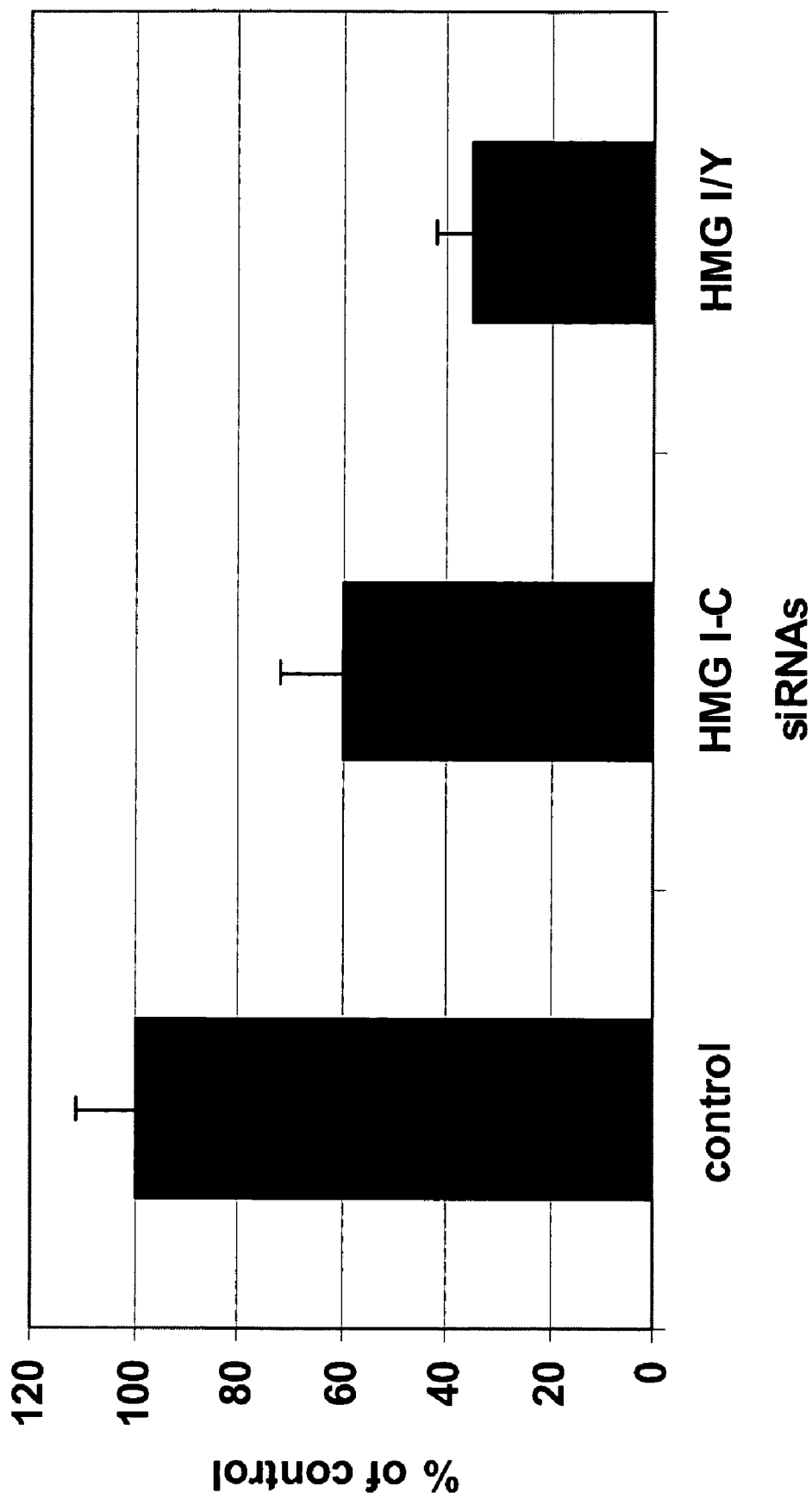
FIG. 8 provides exemplary data showing the effect of HMG I/Y and HMG I-C siRNAs on viral replication of HIV-1 in Magi cells (reverse transcriptase assay).
Figure 9:
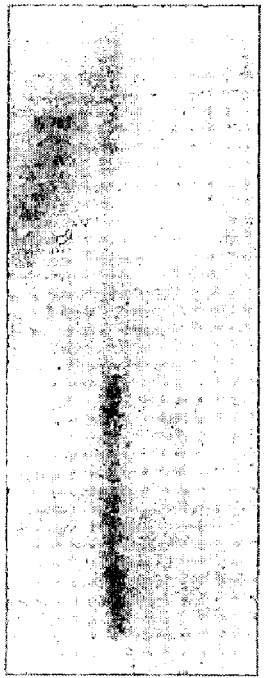
FIG. 9 provides exemplary data that demonstrate that HMG I/Y protein levels are reduced in cells transfected with HMG I/Y siRNA.
Figure 9:
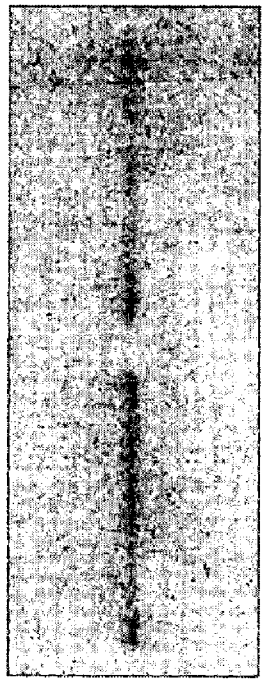
Figure 10:
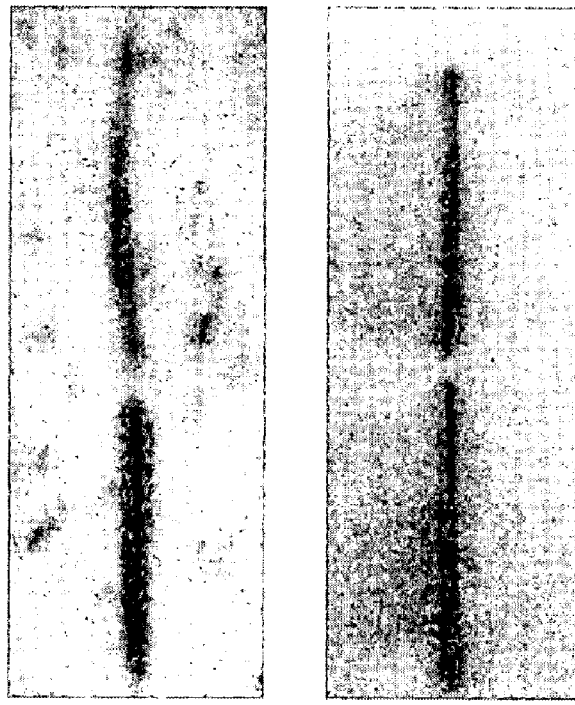
FIG. 10 provides exemplary data that demonstrate that HMG I-C protein levels are reduced in cells transfected with HMG I-C siRNA.

Magi indicator cells were also used to determine the effect of HMG I proteins on the transcription of retroviral genes. Magi cells were transiently transfected with an siRNA targeting HMG I-C or HMG I/Y. A Scramble siRNA was used as a negative control. The results show that the siRNAs targeting both HMG I-C and HMG I/Y inhibited β-gal activity (FIG. 7). Analysis of reverse transcriptase activity in the siRNA-transfected cells showed that RT was reduced in the cells that received HMG I-C and HMG I/Y siRNAs relative to the control cells, suggesting that the viral replication of HIV was significantly inhibited (FIG. 8). Western blot analysis of HMGI/Y and HMG I-C siRNA-treated Magi cells confirmed that levels of the HMG I proteins were reduced in comparison to control cells that were treated with a negative control siRNA that targets luciferase (FIG. 9 and FIG. 10). For the western blot analysis, cells were transiently transfected with the siRNAs targeting HMGI/Y (FIG. 9), HMG I-C (FIG. 10) or firefly luciferase (control siRNA).

Magi cells were lysed 48-60 hours after transfection and analyzed by western blot using antibodies against HMGI/Y, HMG I-C or γ-tubulin proteins. The γ-tubulin levels were used as the loading controls.

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication, patent application, accession number or other reference was specifically and individually indicated to be incorporated by reference.

What is claimed is:

1. A method of identifying a compound that inhibits replication of a retrovirus that infects human cells, the method comprising:

contacting a candidate compound with a nucleic acid that encodes the transcriptional regulator pre-B-cell leukemia transcription factor 1 (Pbx1) under conditions that support transcription of a gene that is operably linked to a Pbx1 responsive element; and determining whether the compound inhibits Pbx1-mediated transcription of said gene, thereby identifying a compound that inhibits replication of the retrovirus.

2. The method of claim 1, further comprising: selecting a compound that binds to the transcriptional regulator nucleic acid.

3. The method of claim 1, wherein the retrovirus is a human immunodeficiency virus.

4. The method of claim 3, wherein the human immunodeficiency virus is HIV-1.

5. The method of claim 1, wherein the step of contacting the candidate compound with the transcriptional regulator nucleic acid comprises incubating the compound with the transcriptional regulator nucleic acid and a reporter construct comprising a Pbx-1 response element.

6. The method of claim 5, wherein the Pbx-1 response element comprises a regulatory sequence from a virus that infects human cells.

7. The method of claim 6, wherein the regulatory sequence comprises an HIV-1 LTR.

8. The method of claim 7, wherein the incubation mixture further comprises tat.

9. The method of claim 8, wherein the incubation comprises contacting the compound with Magi indicator cells that express tat and comprise an HIV-1 LTR reporter construct and the transcriptional regulator nucleic acid.

10. The method of claim 8, wherein the incubation comprises contacting the compound with HeLa cells that express tat and comprise an HIV-1 LTR reporter construct and the transcriptional regulator nucleic acid.

11. The method of claim 1, wherein the transcriptional regulator nucleic acid is comprised in an expression vector.

12. The method of claim 1, wherein the candidate compound is an siRNA.

13. The method of claim 1, wherein the candidate compound is an antisense RNA.

14. The method of claim 1, wherein the Pbx1 is Pbx1b.

* * * * *

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence:Pbx1 siRNA

<400> SEQUENCE: 1
aagccugccu uguuuaaugu g                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence:HMG I/Y
      siRNA

<400> SEQUENCE: 2
aagugccaac accuaagaga c                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence:HMG I-C
      siRNA

<400> SEQUENCE: 3
aagcagcuca aaagaaagca g                                              21
```